United States Patent
Fuisz et al.

[11] Patent Number: 6,062,213
[45] Date of Patent: May 16, 2000

[54] SINGLE UNIT DOSE INHALATION THERAPY DEVICE

[75] Inventors: Richard C. Fuisz, Mclean; B. Arlie Bogue, Broad Run; John F. Levis, Herndon, all of Va.

[73] Assignee: Fuisz Technologies Ltd., Chantilly, Va.

[21] Appl. No.: 09/097,998

[22] Filed: Jun. 16, 1998

[51] Int. Cl.[7] ............................................. A61M 15/00
[52] U.S. Cl. ............................. 128/200.21; 128/200.23; 128/200.25; 128/203.12; 206/219
[58] Field of Search ................... 128/200.23, 203.21, 128/202.25, 202.26, 201.11, 203.15, 203.12, 200.19, 200.21, 200.22; 604/58; 206/219, 222, 562, 221; 366/662

[56] References Cited

U.S. PATENT DOCUMENTS

| | | | |
|---|---|---|---|
| D. 391,369 | 2/1998 | Anderson | D24/110 |
| 496,776 | 5/1893 | Chesebro | 128/200.11 |
| 523,265 | 7/1894 | Chesboro | 128/200.11 |
| 780,077 | 1/1905 | Van Ness | 128/200.11 |
| 2,395,109 | 2/1946 | Fonda | 128/203.21 |
| 2,442,004 | 5/1948 | Hayard-Butt | 128/200.11 |
| 2,546,848 | 3/1951 | Bishop | 128/203.21 |
| 2,696,211 | 12/1954 | O'Gatty | |
| 2,705,007 | 3/1955 | Gerber | 128/200.11 |
| 3,425,414 | 2/1969 | Roche | |
| 3,856,142 | 12/1974 | Vessalo | 206/530 |
| 4,069,819 | 1/1978 | Valentini et al. | 128/203.15 |
| 4,095,596 | 6/1978 | Grayson | 128/200.11 |
| 4,137,914 | 2/1979 | Wetterlin | 128/203.15 |
| 4,454,877 | 6/1984 | Miller et al. | 128/200.21 |
| 4,898,166 | 2/1990 | Rose et al. | 128/205.13 |
| 5,031,800 | 7/1991 | Brunet | 222/153 |
| 5,535,736 | 7/1996 | Jzaw | 128/202.26 |
| 5,678,538 | 10/1997 | Drought | 128/203.15 |
| 5,692,492 | 12/1997 | Bruna et al. | 128/200.23 |
| 5,702,362 | 12/1997 | Herold et al. | 604/58 |
| 5,713,349 | 2/1998 | Keaney | 128/204.23 |
| 5,740,793 | 4/1998 | Hodson et al. | 128/203.15 |
| 5,752,505 | 5/1998 | Ohki et al. | 128/203.15 |
| 5,775,320 | 7/1998 | Patton et al. | 128/200.14 |
| 5,787,881 | 8/1998 | Chawla | 128/203.15 |
| 5,787,884 | 8/1998 | Tovey | 128/206.11 |
| 5,819,730 | 10/1998 | Stone et al. | 128/203.21 |
| 5,884,621 | 4/1999 | Matsugi et al. | 128/203.15 |
| 5,894,841 | 4/1999 | Voges | 128/203.12 |

*Primary Examiner*—Aaron J. Lewis
*Assistant Examiner*—V. Srivastava
*Attorney, Agent, or Firm*—John F. Levis

[57] ABSTRACT

A single dose device for delivering an active substance via the nostrils or mouth is portable, lightweight, compact and easily hand-held.

11 Claims, 2 Drawing Sheets

SINGLE UNIT DOSE INHALATION THERAPY DEVICE

FIELD OF THE INVENTION

The present invention relates to a device and method for administering an active substance to the body, and more particularly, to a single-dose inhalation therapy device which is convenient to use, compact, lightweight and portable.

BACKGROUND OF THE INVENTION

Today, many devices are available for administering active substances to the body, in particular the throat, lungs or sinuses, via the nose (nostrils) or mouth. These devices may include containers in various forms for delivering OTC and prescription medicaments and other preparations. The user inserts one end of the device container into the nose or mouth, and then squeezes the container, or presses or pushes a tab to break a seal and thereby release the active substance into the nose or mouth. At the same time, the user will inhale, i.e. take a big breath, thereby pulling the medicine into the sinus cavity, throat or lungs.

Unfortunately, many of these devices have been formulated to contain multi-dose preparations. As such, they are complex and cumbersome to use. In one such device several unit dosages are individually sealed in blister packs mounted on a rotating disc. The user breaks a seal on the blister pack each time access to a single dose is required. Often times, however, the consumer desires not to tote around more medicine than he or she will need for a few hours. In other embodiments of devices presently available, a squeeze-type bottle is used to deliver successive dosages of an active to the body. The problem with these latter devices is that for preparations whose delivery must be precise, it is difficult to regulate delivery by the mere act of squeezing the bottle for delivery of dosages.

What is needed, therefore, is a single dose container for delivering an active to the body via the nose or mouth. The device should be simple to activate, lightweight and portable. The container should also be compact, non-permeable, and self-contained. It is further desirable to equip the device with a mechanism which is highly effective at either passive or active movement (or both), hereinafter defined, of the active into the body. In addition to the active substance, the container should also house any solid, liquid or gaseous carrier or any delivery system necessary to contain and administer the active.

SUMMARY OF THE INVENTION

The present invention is directed to a single dose inhalation therapy device which is useful in delivering a medicament or some other preparation to the sinus, lungs or throat. The device is preferably compact, hand-held, portable, easy to use and disposable.

In another embodiment of the invention there is provided a portable, hand-held single-dose device for delivering an active substance via the nostrils or mouth which comprises an outer container and an inner container. At least a portion of the inner container is spaced apart from and surrounded by the outer container. At least one of the outer and inner containers are breakably sealed and will house an active substance. The device further comprises at least one activation means for access to the active substance, with the activation means being in communication with the interior of at least one of the inner and outer containers.

The invention further includes a method of administering an active substance to the body via the nose or mouth which comprises the activation of the single unit dose inhalation therapy device described herein according to its various embodiments.

DETAILED DESCRIPTION OF THE PREFERRED EMBODIMENTS

Figure 1A:
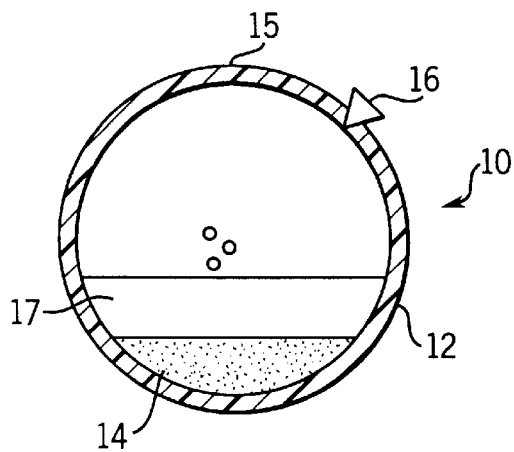
FIG. 1A is an plan view illustration of the device of the invention according to one embodiment.

Referring now to the drawings, wherein like numerals represent like components throughout the various embodiments, FIG. 1A is an illustration of the device according to one embodiment of the invention. A single dose inhalation therapy device 10 has a breakably sealed container 12 at least partially filed with an active substance 14. The container 12 is comprised of any substantially durable material, either rigid, or more preferably flexible and collapsible. The material is also substantially non-permeable by liquids and gas, and is non-reactive. Various thermoplastic polymers and metal alloys known to the skilled artisan may serve as the material for the container. The container 12 may be surrounded by an optional removable covering 15 for protection and also to indicate whether the device has been spent. The device 10 according to all its embodiments should be lightweight and of a size and shape sufficient for easy manipulation and use by the consumer. The device 10 should be easily transportable in, for example, a pocket or purse. It should furthermore be lightweight, weighing up to about a few ounces at most. In a preferred embodiment shown in FIG. 1A, the device 10 is configured like a spheroid within the range of about one-quarter to three inches in diameter. A spheroidal shape permits the device 10 of the invention to contain a higher internal pressure.

One or more activation means 16 are also provided to enable the user to access the active substance 14. Such activation means may be selected from the group consisting of push- and pull-type mechanisms, as well as combinations thereof. These could include, for example, a pin, needle or pull tab which is depressed through or is pulled off the container 12 to thereby puncture or pierce the container. A hole through the container 12 is thus provided by which the user of the device 10 may place his nostril or mouth and inhale to take in the active substance 14. A variety of other activation means 16 available to the skilled artisan could also be utilized which would open or activate the device 10 of the invention, and thereby permit access to the active substance. In addition, the container 12 could also be sheared by biting down at a prescribed location. An optional protector (not shown), preferably of a rigid, durable material, could be mounted on or over the activation means 16 to prevent unintentional activation by the consumer. A see-through plastic cap could function as the protector.

Figure 1B:
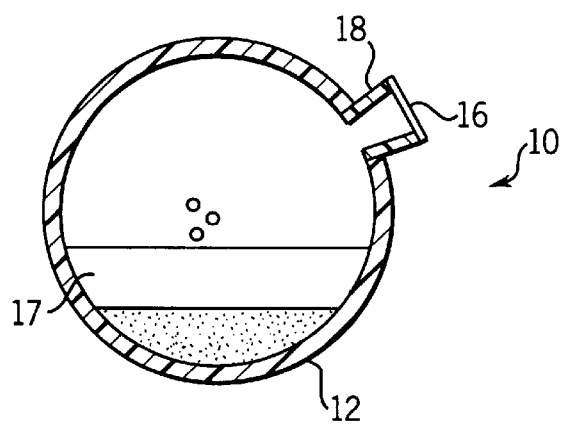
FIG. 1B is a plan view of a further embodiment of the device shown in FIG. 1A.

Referring also to FIG. 1B, the device 10 of the present invention may contain one or more delivery means selected from the group consisting of proactive delivery means and passive delivery means, as well as one or more combinations thereof. By "proactive delivery means" it is meant that the container 12 will house some means to physically transport or propel a single dose of the active substance 14 from the device into the internal cavity. Proactive delivery means will therefore include such propellant means as gases, vapors and liquids which are desirably under pressure in the device 10 itself. In one embodiment, compressed gas will serve as a proactive delivery means 17. This is shown in both FIGS. 1A and 1B. Any inert, biocompatible gas or combination of gases could function as the delivery means 17. Of these, nitrogen and carbon dioxide may be preferred. These are readily available and are relatively cheap. Activating the device via the activation means 16 would permit movement of the proactive delivery means 17 towards an area of lower pressure outside the device 10, thereby moving the active substance 14 outwards as well.

Also within the scope of the invention is the utilization of super-saturated dissolved gas as a proactive delivery means 17. Carbon dioxide dissolved in water would be one preferred example of super-saturated dissolved gas. Agitation of the device 10 would create internal pressure which could then be released once the activation means 16 was released. The emerging gas would then carry or propel the active substance 14 from the device. An analogy is drawn to the release of liquid (and gas) once the tab on an agitated can of warm soda pop is pulled.

Another type of proactive delivery means 17 would involve a chemical reaction (to generate gas). For example, citric acid and sodium bicarbonate in the presence of water or acetic acid to generate carbon dioxide gas is just one example of a suitable chemical reaction. The individual reactants citric acid and sodium bicarbonate could be housed in separate, divided compartments within the container 12 of the device 10. Once a seal separating the reactants was punctured or otherwise released, as for example via the activation means 16, then the chemicals could mix and react, thereby generating the necessary gas or gasses to propel the active substance 14 outwards from the device and into the mouth or nostrils.

Vaporizable liquid could also serve as a proactive delivery means 17. Those skilled in the art may find any other biocompatible liquids or combinations thereof to be useful as well as the proactive delivery means 17, so long as these had a high enough vapor pressure at room temperature such that it would vaporize thoroughly upon activation. Possible candidates would therefore include certain types of nontoxic fluorocarbons.

It may also be possible to incorporate aerosol mechanisms into the design of the device 10. These would include means for dispensing one or more of the foregoing propellant gases and/or liquids as the proactive delivery means 17 together with the active substance 14. The aerosol mechanism could also be utilized as the activation means 16 to spray the active substance 14 into the internal cavity of the user.

Also highly feasible is a proactive delivery means 17 which is structural in design. One embodiment of the proactive delivery means could therefore include a propulsion mechanism or a combination of physical segments of structural material in or on the device which would physically propel the active forward. A spring loaded shoveling mechanism as the proactive delivery means is therefore one option. The physical material could be comprised of any substantially strong and durable inert metal, polymer or alloy. Once activated, as for example by depressing a button located on the container 12, the proactive delivery means 17 would physically "shovel" or push the active substance 14 into the recipient's mouth or nostrils. The propulsion mechanism should provide sufficient force so that the active substance is quickly moved to the back of the throat or nostrils. If the force is too weak, an undesirable dissipation of the active in the front of the mouth or nostrils will occur. If the force is too strong, damage to the user's internal cavities could result.

Referring again to FIG. 1B, a passive delivery means 18 could also be incorporated into the device 10 of the invention to aid in delivering the active substance 14 to the user. Unlike the foregoing proactive delivery means which would physically move the active substance 14, the "passive delivery means" would instead utilize an inherent structural design and shape of at least a portion of the device 10 to facilitate the outward movement of the active substance. Thus, the container 12 could be shaped to permit ease of insertion of at least a portion thereof into the nose or mouth, and thereby allow for easier movement of the active substance. As shown in FIG. 1B, the container 12 could be designed with a protruding and expanding rounded segment, with the latter end serving as the part to enter the nose or mouth. By removing a seal functioning as the activation means 16 affixed to one end of the passive delivery means 18, and then inhaling or sucking on the opening thereby revealed, an outward pressure flow would be created which would facilitate movement of the active substance 14 into the nostrils or mouth. Due to the expanding segment design of the passive delivery means 18 shown in FIG. 1B, the active substance would decrease speed as it entered the recipient's mouth, so as not to overwhelm the user or cause choking. (In all embodiments herein, the design and construct of the device of the invention should permit the attainment of generally accepted velocities of the active substance for entering the internal cavities of the user.) Those skilled in the art will recognize, and as FIG. 1B illustrates, a passive delivery means 18 could be utilized alone, or in combination with one or more of the heretofore described proactive delivery means 17.

Figure 2:
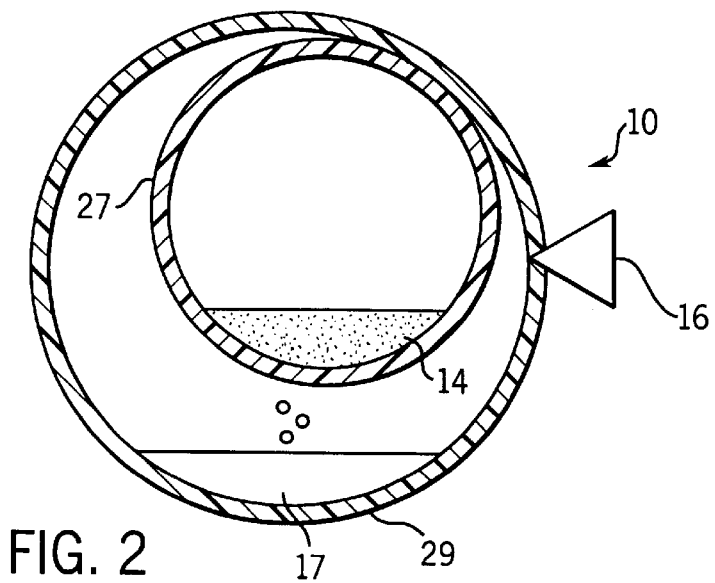
FIG. 2 is a plan view of another embodiment of the device of shown in FIG. 1A.

Referring now to FIG. 2, an alternative embodiment of the device 10 shown in FIG. 1A would have the device 10 of the invention in the form of two or more containers, with an inner container 27 essentially surrounded by or contained within an outer container 29. It is highly desirable that both the inner and outer containers 27, 29 be in substantially spheroidal in shape. As shown in FIG. 2, at least a portion of the inner container 27 may be contiguous or coextensive with at least a portion of the outer container 29. At least one of the containers, and preferably the inner container 27, could house the active substance 14, while at least one of the other containers, preferably the outer container 29, could house a proactive delivery means 17, such as a propellant means, e.g. carbon dioxide or other substantially inert gas, either free or supersaturated in a non-toxic liquid. The inner container 27 would also desirably be collapsible upon activation of the device 10 to further facilitate release of the active substance 14.

As shown in FIG. 2, activation means 16 would provide access to the inner container 27, preferably by puncturing a hole at the segment of the device 10 where the inner container 27 and the outer container 29 are contiguous or coextensive. The hole thereby revealed by the activation means 16 would allow the user access to the active substance 14 as container 27 collapsed. The proactive delivery means 17 contained within the outer sphere 29 would assist in pushing the active substance 14 out of the inner container 27 as the latter collapsed. As the consumer sucked on the hole revealed by the deployed activation means 16 the active substance 14 would enter the user's mouth. The proactive delivery means 17 would most desirably not escape the device, however, as egress would be blocked by the inner container 27.

Figure 3:
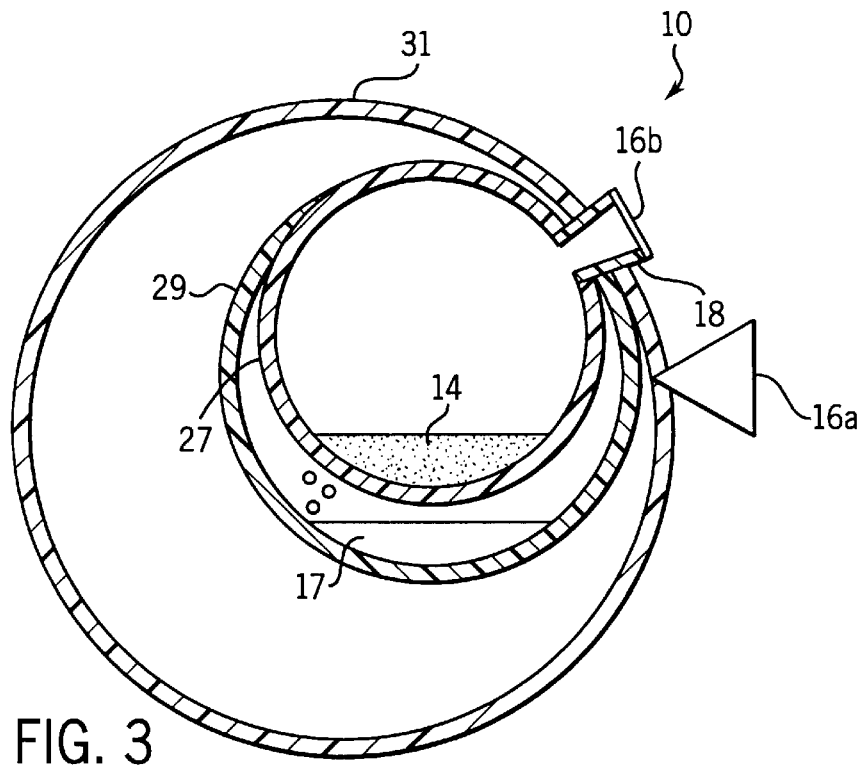
FIG. 3 is a plan view of a further embodiment of the device shown in FIGS. 1B and 2.

Referring now to FIG. 3, there is shown a further embodiment of the device 10 set forth in FIGS. 1B and 2. In FIG. 3 there is an optional third container or shell 31 which surrounds the inner container 27 and the outer container 29. At least a portion of the shell 31 is contiguous or coextensive with at least a portion of one or both of the inner and outer containers 27, 29. The shell 31 reveals an air entrainment space 33 around the outer container 29. As shown in FIG. 3, the air entrainment space 33 preferably has a point of contact with the inner container 27. Upon activation of the device 10, this space would provide air entrainment, thereby facilitating movement of the active substance 14 from the device 10 as the user inhaled. A first activation means 16a, which would essentially be a rupturing or puncturing means to include a pin or needle on top of the device 10, could be depressed to puncture or rupture the shell 31 and the inner container 27 and thereby activate the device. As further shown in FIG. 3, the device 10 could also utilize a passive delivery means 18 for inhalation access. A removable seal 16b would then function as a second activation means on the passive delivery means 18. This second activation means 16b could be deployed once the first activation means 16a had been activated. The consumer's finger could be placed over the hole revealed by the deployed activation means 16a, if need be. The active substance 14 would then be released and moved into the body cavity of the individual by the action of sucking or inhaling, preferably over the passive delivery means 18, which would in turn be assisted by the action, e.g. fizzing, of the proactive delivery means 17 as it contacted the collapsing inner container 27. As previously mentioned, the air entrainment space 33 would further assist the movement of the active substance 14 out of the device as the consumer inhaled or sucked in.

Other components which may be included as part of the device of the invention could include a mounted whistle, or some other means of sound-making, which would notify the user that the device was expended, i.e. all the active substance therein had been released.

Figure 4:
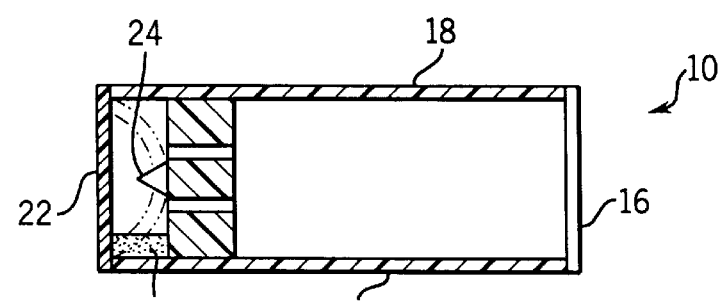
FIG. 4 is a plan view of another embodiment of the device of the invention.

Referring now to FIG. 4, another possible design mechanism of the device 10 of the invention is shown. Means to release the active substance 14 could include a diaphragm 22 with a mounted puncture tool 24 at or near the distal end of the device. The user would insert the opposite, proximal end of the passive delivery means 18 into the mouth or nostrils after unsealing the device 10 by removing the activation means 16, and through the action of inhaling or sucking would cause the substantially flexible diaphragm 22 at the distal end to contact the puncture tool 24, thereby rupturing the diaphragm, and allowing the active to be released.

Figure 5:
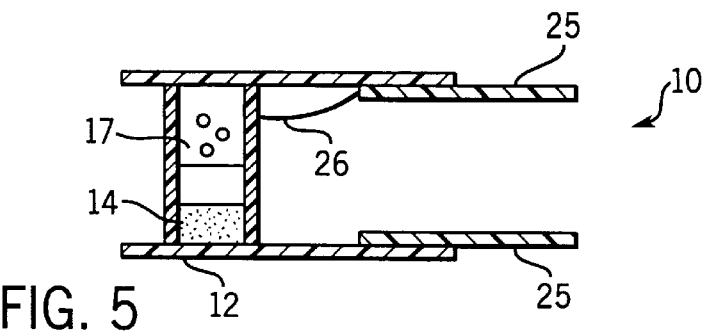
FIG. 5 is a plan view of an additional embodiment of the device of the invention.

In FIG. 5 there is shown the device 10 in still a further embodiment. A retractably compacted "telescopic" internal container 25 is provided inside the container 12 as an additional embodiment of the invention. This telescopic internal container 25 could be pulled outwards by the user to activate the device by rupturing an internal seal via flexible attachment 22, and permitting release of the active substance 14 and an optional proactive delivery means 17 to then be inhaled by the recipient.

Those skilled in the art will recognize that the device of the invention could incorporate any or all of the heretofore described features into its overall structure.

Overall, it is the goal of the invention according to the various embodiments herein set forth that the device be such that the active is capable of release in a precise, measured, easy-to-use single dose form. The operation of the device should, therefore, be "idiot-proof." The overall design of the device of the invention should further these ends.

A non-limiting listing of suitable preparations which could serve as active substances to be included in the single dose device of the invention are among the following: antitussives, antihistamines, decongestants, alkaloids, mineral supplements, laxatives, vitamins, e.g. vitamin D3, antacids, ion exchange resins, anti-cholesterolemics, antilipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, antiinfectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, antiemetics, anti-nauseants, anti-convulsants, neuromuscular drugs, hyper- and hypoglycemic agents, thyroid and antithyroid preparation, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs, antismoking preparations such as nicotine, and mixtures thereof.

The foregoing active substance(s) could be admixed with one or more suitable pharmaceutical vehicles or inert substances in the form of powders, liquids or gases, all of which are well known to the skilled artisan.

While the invention has been described in each of its various embodiments, it is expected that certain modifications thereto may be effected by those skilled in the art without departing from the invention's true spirit and scope as set forth in the specification herein and the accompanying claims.

We claim:

1. A portable hand-held single-dose device for delivering an active substance via the nostrils or mouth, said device having an outer container and an inner container such that at least a portion of said inner container is spaced apart from and surrounded by said outer container, and wherein said inner and outer containers are substantially spheroidal and partially co-extensive, said outer and inner container being breakably sealed and said inner container housing an active substance and said outer container housing a propellant, said device further comprising at least one activation means for access to said active substance, said activation means being in communication with the interior of said outer container and said inner container, whereupon said device is rendered spent upon activation of said activation means.

2. The device of claim 1, wherein said proactive delivery means is at least one propellant selected from the group consisting of gases, liquids, vapors and combinations thereof.

3. The device of claim 1, further comprising a passive delivery means.

4. The device of claim 1, further comprising a shell surrounding said inner and outer containers for providing air entrainment space.

5. A method of delivering an active substance to the body via the nostrils or mouth which comprises activating the device of claim 1.

6. A method of delivering an active substance to the body via the nostrils or mouth which comprises activating the device of claim 3.

7. A method of delivering an active substance to the body via the nostrils or mouth which comprises activating the device of claim 4.

8. The device of claim 1, wherein said active is at least one member selected from the group consisting of: antitussives, antihistamines, decongestants, alkaloids, mineral supplements, laxatives, vitamins, e.g. vitamin D3, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and anti-thyroid preparation, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs, anti-smoking preparations such as nicotine, and mixtures thereof.

9. The device of claim 1, wherein at least one of said inner and outer containers is flexible and collapsible.

10. The device of claim 1, wherein said device is about one-quarter to three inches in diameter.

11. The device of claim 4, wherein said device is about one-quarter to three inches in diameter.

* * * * *